(12) United States Patent
Highley (10) Patent No.: US 10,998,102 B1
(45) Date of Patent: May 4, 2021

(54) SYSTEMS FOR MANAGING RESISTANT HYPERTENSION

(71) Applicant: Analytics4medicine LLC, Burien, WA (US)

(72) Inventor: Robert D Highley, Burien, WA (US)

(73) Assignee: ANALYTICS4MEDICINE LLC, Burien, WA (US)

( * ) Notice: Subject to any disclaimer, the term of this patent is extended or adjusted under 35 U.S.C. 154(b) by 0 days.

(21) Appl. No.: 17/075,634

(22) Filed: Oct. 20, 2020

Related U.S. Application Data

(60) Provisional application No. 63/094,284, filed on Oct. 20, 2020.

(51) Int. Cl.
| | |
|---|---|
| *G16H 50/20* | (2018.01) |
| *G16H 40/20* | (2018.01) |
| *A61B 5/00* | (2006.01) |
| *A61B 5/145* | (2006.01) |
| *G16H 10/20* | (2018.01) |

(Continued)

(52) U.S. Cl.
CPC ............ *G16H 50/20* (2018.01); *A61B 5/021* (2013.01); *A61B 5/14546* (2013.01); *A61B 5/4842* (2013.01); *A61B 5/4848* (2013.01); *A61B 5/7267* (2013.01); *A61B 5/742* (2013.01); *A61B 5/7405* (2013.01); *A61B 5/746* (2013.01); *G16H 10/20* (2018.01); *G16H 10/40* (2018.01); *G16H 40/20* (2018.01); *G16H 50/30* (2018.01);
(Continued)

(58) Field of Classification Search
CPC ........ G16H 50/20; G16H 70/40; G16H 10/40; G16H 50/30; G16H 70/60; G16H 10/20; G16H 50/50; G16H 50/70; G16H 40/20; A61B 5/7405; A61B 5/742; A61B 5/7267; A61B 5/021; A61B 5/746; A61B 5/4842; A61B 5/14546; A61B 5/4848
See application file for complete search history.

(56) References Cited

U.S. PATENT DOCUMENTS

| | | | | |
|---|---|---|---|---|
| 2011/0202486 | A1* | 8/2011 | Fung | ..................... G16H 50/30 706/12 |
| 2020/0147113 | A1* | 5/2020 | Lifton | ................ A61K 31/7048 |
| 2020/0397972 | A1* | 12/2020 | Ku | ..................... A61M 1/3663 |

FOREIGN PATENT DOCUMENTS

WO    WQ-2020002478 A1 *  1/2020    ............. G16H 50/20

OTHER PUBLICATIONS

Gaddam et al., Characterization of Resistant Hypertension, Jun. 9, 2008, Arch Intern Med, vol. 168, No. 11, pp. 1159-1164. (Year: 2008).*
Spence, Lessons From Africa: The Importance of Measuring Plasma Renin and Aldosterone in Resistant Hypertension, 2012, Canadian Journal of Cardiology, pp. 254-257. (Year: 2012).*

(Continued)

*Primary Examiner* — Christopher L Gilligan
(74) *Attorney, Agent, or Firm* — Naira Simmons; FisherBroyles, LLP (57) ABSTRACT

Disclosed herein is a clinical decision support tool designed to address problems with blood pressure control, compliance with frequent monitoring requirements, diagnostic inertia, therapeutic inertia, and disease misclassification by using peak diurnal blood pressure. In some aspects, the systems and processes of the disclosure sort secondary hypertension conditions from a multitude of other underlying factors. The systems of the disclosure can use a drug sequencing algorithm based on age, ethnicity, associated-disease, renin/ aldosterone levels, and other factors to evaluate their effects on blood pressure control, provider time, and provider/ patient satisfaction.

28 Claims, 1 Drawing Sheet

(51) Int. Cl.
  *G16H 50/30* (2018.01)
  *G16H 10/40* (2018.01)
  *G16H 70/40* (2018.01)
  *G16H 50/70* (2018.01)
  *G16H 70/60* (2018.01)
  *G16H 50/50* (2018.01)
  *A61B 5/021* (2006.01)

(52) U.S. Cl.
  CPC ............. *G16H 50/50* (2018.01); *G16H 50/70* (2018.01); *G16H 70/40* (2018.01); *G16H 70/60* (2018.01)

(56) References Cited

OTHER PUBLICATIONS

Zhang et al., Predicting blood pressure from physiological index data using the SVR algorithm, 2019, BMC Bioinformatics, pp. 1-15. (Year: 2019).*

Funder et al., Case Detection, Diagnosis, and Treatment of Patients with Primary Aldosteronism: An Endocrine Society Clinical Practice Guideline, Sep. 2008, Journal of Clinical Endocrinology & Metabolism, pp. 3266-3281. (Year: 2008).*

NHANES 2015-2016: Blood Pressure Data Documentation, Codebook, and Frequencies (cdc.gov), National Health and Nutrition Examination Survey, 2015-2016 Data Documentation, Codebook, and Frequencies, Blood Pressure (BPX_I), Data File: BPX_I.xpt, First Published: Sep. 2017, https://wwwn.cdc/Nchs/Nhanes/2015-2016/BPX_I.htm.

\* cited by examiner

SYSTEMS FOR MANAGING RESISTANT HYPERTENSION

GOVERNMENT FUNDING

This work was supported by Telemedicine and Advanced Technology Research Center (TATRC), AMEDD Advanced Medical Technology Initiative (AAMTI), Fort Detrick, Md. Software & technical support was provided by Analytics4Medicine Seattle Wash.

BACKGROUND

Blood pressure is the force of blood pushing against the artery walls. The force is generated by each heartbeat as blood is pumped from the heart into the blood vessels. The size, tone and elasticity of the arteries walls also affect blood pressure. The kidneys regulate blood pressure as well by regulating the amount of fluid and salt in the body.

Hypertension is defined when the average arterial blood pressure during a normal day is 130/80 mmHg or higher. Hypertension progressively damages the walls of large arteries (aorta, carotids) as well as smaller ones (cerebral, coronary, renal, retinal) and makes the heart work harder to get blood pumped through the body. Many difficulties exist in managing hypertension, specially because one can have hypertension without having visible symptoms.

SUMMARY

Provided herein is a clinical decision support (CDS) system for a subject afflicted by resistant hypertension, the CDS system comprising a non-transitory computer readable medium storing instructions that, when executed by at least one programmable processor, cause the at least one programmable processor to perform operations comprising: receiving, by a computing device, a set of data consisting of at least five blood pressure measurements of the subject; classifying the data into one of two bins consisting of controlled or uncontrolled by a computer implemented method selected from a linguistic method and a machine learning method; and outputting the classification result, thereby providing clinical decision support for the identification of resistant hypertension in the subject. In preferred embodiments, a computing device, further receives a result from a renin test of the subject, a result from an aldosterone test of the subject. In most preferred embodiments, the system receives both and the data received is further structured by a matrix that groups the results from the renin test of the subject and the result from the aldosterone test of the subject into one of nine-possible combinations of low, normal, and high renin and aldosterone levels. The system then combines the results of the pdBP received, the renin test, and the aldosterone test and provides a differential diagnosis of hypertension. The data can be further structured as to provide a listing of one or more drugs for each specific differential diagnosis of hypertension.

The one or more differential diagnosis of hypertension for a low renin-high aldosterone combination can be Conn's syndrome, aldosterone producing adenoma, unilateral adrenal hyperplasia, familial hyperaldosteronism 1-2-3), adrenocortical carcinomas, ectopic aldosterone secreting tumors, simple virilizing form of partial 21-hydroxylase, or enzyme deficiency congenital adrenal hyperplasia.

The one or more differential diagnosis of hypertension for a low renin-normal aldosterone combination can be Chronic Kidney Disease, Low renin primary HTN, Syndrome of Supine HTN-OH, or Pheochromocytoma.

The one or more differential diagnosis of hypertension for a low renin-low aldosterone combination can be Congenital Adrenal Hyperplasia due to 11p-hydroxylase (CYP11B1) deficiency), Congenital Adrenal Hyperplasia due to 17α-hydroxylase (CYP17) deficiency, DOC producing Tumors, 18-Hydroxy-1-deoxycorticosterone (18-OH-DOC) aldosteronoma, Mineralocorticoid receptor activating mutation, Geller's Syndrome, Pregnancy exacerbated hypertension, Pseudohypoaldosteronism Type II/PHA II, Gordon's Syndrome, Chloride shunt syndrome, Mineralocorticoid resistant hyperkalemia, Kidney Disease (Glomerular or Tubular disease), Liddle's Syndrome, Pseudohypoaldosteronism Type II/PHA II, Weinstein-Spitzer Syndrome, Subtype 3 Renal Tubular Acidosis, Medication Effect (NSAIDs, Cox 2 inhibitors), Pheochromocytoma, Adducin Polymorphism, Endogenous Ouabain, Exogenous Source, GIP induced Cushing's, Cushing's Disease, Cushing's Syndrome, Iatrogenic Cushing's, Syndrome.Pan-neoplastic Cushing's syndrome, Generalized Glucocorticoid Resistance (Chrousos Syndrome), Congenital Apparent Mineralocorticoid Excess (AME), Acquired AME/Pseudohyperaldosteronism, Small cell cancer of the lung (éACTH), Bronchial carcinoids (éACTH), and Pheochromocytoma.

The one or more differential diagnosis of hypertension for a normal renin-low aldosterone combination can be Congenital Adrenal Hyperplasia due to 1p-hydroxylase (CYP11B1) deficiency), Congenital Adrenal Hyperplasia due to 17α-hydroxylase (CYP17) deficiency, DOC producing Tumors, 18-Hydroxy-ll-deoxycorticosterone (18-OH-DOC) aldosteronoma, Mineralocorticoid receptor activating mutation, Geller's Syndrome, Pregnancy exacerbated hypertension, Pseudohypoaldosteronism Type II/PHA II, Gordon's Syndrome, Chloride shunt syndrome, Mineralocorticoid resistant hyperkalemia, Kidney Disease (Glomerular or Tubular disease), Liddle's Syndrome, Pseudohypoaldosteronism Type II/PHA II, Weinstein-Spitzer Syndrome, Subtype 3 Renal Tubular Acidosis IV, Medication Effect (NSAIDs, Cox 2 inhibitors), Pheochromocytoma, Adducin Polymorphism, Endogenous Ouabain, Exogenous Source, GIP induced Cushing's, Cushing's Disease, Cushing's Syndrome, Iatrogenic Cushing's Syndrome, Pan-neoplastic Cushing's syndrome, Generalized Glucocorticoid Resistance (Chrousos Syndrome), Chrorous Syndrome, Congenital Apparent Mineralocorticoid Excess (AME), Acquired AMF/Pseudohyperaldosteronism, Small cell cancer of the lung (éACTH & cortisol), Bronchial carcinoids (éACTH & cortisol), or Pheochromocytoma.

The one or more differential diagnosis of hypertension for a normal renin-normal aldosterone combination can be Acromegaly, AD HTN with brachydactyly, Drugs, Hyperparathyroidism, Hyperthyroidism, Hypoparathyroidism, Hypothyroidism, Increased Intercranial Pressure, Insomnia, Sleep Apnea, Primary/Essential HTN, or Pheochromocytoma.

The one or more differential diagnosis of hypertension for a normal renin-high aldosterone combination can be APA/Conn's Syndrome, Bilateral Adrenal Hyperplasia, Unilateral Adrenal Hyperplasia, Ectopic Aldosterone Tumor, Familial Hyperaldosteronism 1, Familial Hyperaldosteronism 2, Familial Hyperaldosteronism 3, or Pheochromocytoma.

The one or more differential diagnosis of hypertension for a high renin-low aldosterone combination can be Coarctation of the Aorta, Diabetic Nephropathy, Glomerulonephritis, Glomerulosclerosis, Middle Aortic Syndrome, Polycystic Kidneys, Renal artery Fibromuscular Hyperplasia, Renal Artery Dissection, Renal Artery Emboli/Infarction, Renal Artery Stenosis, Renin secreting Tumors, Takayasu's Arteritis, or Pheochromocytoma.

The one or more differential diagnosis of hypertension for a high renin-normal aldosterone combination can be Coarctation of the Aorta, Diabetic Nephropathy, Glomerulonephritis, Glomerulosclerosis, Middle Aortic Syndrome, Polycystic Kidneys, Renal artery Fibromuscular Hyperplasia, Renal Artery Dissection, Renal Artery Emboli/Infarction, Renal Artery Stenosis, Renin secreting Tumors, Takayasu's Arteritis, or Pheochromocytoma.

The one or more differential diagnosis of hypertension for a high renin-high aldosterone combination can be Coarctation of the Aorta, Diabetic Nephropathy, Glomerulonephritis, Glomerulosclerosis, Middle Aortic Syndrome, Polycystic Kidneys, Renal artery Fibromuscular Hyperplasia, Renal Artery Dissection, Renal Artery Emboli/Infarction, Renal Artery Stenosis, Renin secreting Tumors, Takayasu's Arteritis, Toxemia of Pregnancy, and Pheochromocytoma.

In preferred embodiments the system supports continued monitoring of the subject. Thus, the set of data is preferably received at regular intervals—which can be daily, twice-daily, weekly, or biweekly, monthly, and bimonthly—over a period-of-time. The period-of-time can be over a course of at least 2 days, at least 5 days, at least 10 days, at least 14 days, or over the lifetime of the subject. In many instances, the set of data comprises at least two peak diurnal blood pressure measurements. In some cases the at least two peak diurnal blood pressure measurements in the at least six peak diurnal blood pressure measurements comprises a peak morning blood pressure measurement (peak am) and a peak afternoon blood pressure measurement (peak pm). In other instances, the at least two peak diurnal blood pressure measurements in the at least six peak diurnal blood pressure measurements comprises a peak morning blood pressure measurement from day 1 and a peak morning blood pressure measurement from day 2. In most preferred embodiments, the at least six peak blood pressure measurements are from consecutive days.

In further embodiments, the computing device provides the set of data consisting of blood pressure measurements of the subject to a health care provider. In other embodiments, the at least one programmable processor is configured to query a database of electronic records to retrieve an age, an ethnicity, or a weight, or the subject. In some instances the system is further programmed to use a drug sequencing algorithm based on age, ethnicity, and one of the combinations of low, normal, and high renin and aldosterone levels from the subject for annotating the set of data with a differential diagnosis for secondary hypertension.

Most preferably, the results achieved with the CDST described herein is displayed on a graphical user interface. The result can comprise one or a combination of two or more of text, color, imagery, or sound. Additionally, the outputting operation for displaying the results can further send an alert to an end-user if the results of the classification are "uncontrolled" and the patient had a previous result of "controlled". The alert can be in the form of a visual or audio signal that is transmitted to a computing device selected from a personal computer, a tablet computer, and a smart phone. The alert can be manifested as any of an email, a text message, a voice message, or sound.

In some instances, the system is trained with a classifier and the classifying step is performed by applying a classifier selected from the group consisting of a Baysean, Machine learning, a pre-trained support vector machine (SVM), a log-likelihood ratio, Bayes factor, or Kullback-Leibler Divergence. In on specific embodiment, the classifier was trained on a training set comprising or consisting of a set of 54 subjects from a population of subjects afflicted with hypertension. In a most preferred embodiment, the training set was further annotated with differential diagnosis to sort to sort secondary hypertension.

Also contemplated by the disclosure is a method for the identification of hypertension for subjects who are candidates for surgery, the method comprising use of the system described herein.

Also contemplated by the disclosure is a system comprising the CDS system of claim 1 operatively linked to one or more databases of electronic medical records or clinical data, or both.

BRIEF DESCRIPTION OF THE DRAWINGS

The foregoing and other features and advantages of the present invention will be more fully understood from the following detailed description of illustrative embodiments taken in conjunction with the accompanying drawings in which.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

All of the functionalities described in connection with one embodiment of the systems and methods described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Definitions and Abbreviations

As used herein, the renin-aldosterone system is abbreviated "RAS." It is a hormone system within the body that is essential for the regulation of blood pressure and fluid balance. The system is mainly comprised of the hormones renin and aldosterone. The system can also include the hormone angiotensin II, in such instances the system is referred to as the Renin-Angiotensin-Aldosterone System (RAAS).

As used herein, the peak diurnal blood pressure is abbreviated "pdBP."

As used herein, apparent resistant hypertension is abbreviated "aHTN."

Note that as used herein and in the appended claims, the singular forms "a," "an," and "the" include plural referents unless the context clearly dictates otherwise.

As used herein, the term "resistant hypertension" generally refers to blood pressure not at goal treated with 3 or more medications (one of which is a diuretic) for more than one month. Hypertension can be considered resistant when blood pressure remains above a specific goal for a subject's age, weight, and gender, generally above a range of 130/80 mmHg. Hypertension that requires four or more medications to be controlled it is also called resistant hypertension. "Uncontrolled hypertension" refers to blood pressure above individualized BP goals. It is made up of resistant hypertension and apparent resistant hypertension.

Where a range of values is provided, e.g., range of blood pressures, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

Hypertension (HTN) is the primary risk factor for cardiovascular disease worldwide. By 2030, over 23.6 million deaths globally are expected to be attributed to cardiovascular diseases. Cardiovascular conditions cost over $350 billion/year in the U.S. alone, of which $55.9 billion is associated with HTN. Controlling HTN increases quality of life and may result in cost savings up to $10,249 per person per year in the USA. Management of HTN remains an office-based, discretionary, sequential drug, trial-and-error approach that has not changed in over 50 years. Using this approach, less than half of patients are controlled, yet the effectiveness of this approach has not been systematically evaluated.

Hypertension is difficult to control for multiple reasons, including: 1) poor treatment adherence in a relatively asymptomatic disease, 2) lifestyle issues such as obesity, excess dietary salt and alcohol, licorice, and some medications, 3) therapeutic inertia, failure to intensify therapy when targets are not met, 4) diagnostic inertia, overlooking secondary causes, and 5) shifting definitions as guideline recommended blood pressure (BP) targets lower over time, making goals harder to achieve.

In the general population, rates of BP are better in those groups with healthcare insurance, such as the military. Hypertension prevalence among active duty U.S. military service members (SM) is not widely known. However, available literature indicates that almost 20% (240,000) of active duty SM have HTN, which makes it one of the most frequent chronic conditions among SM.6 Service members with severe combat injuries and post-traumatic stress disorder were more likely to develop HTN, and Army SM (30%) were less likely to have optimal BPs than civilians (55%) despite being a relatively younger population. Data from the 2018 National Health and Nutrition Examination suggested that adults of 18 to 39 years old were less likely to have their HTN controlled compared to persons age 60 or older. Reports of at least one chronic condition in SM ranges from 31% to 46%, the most frequent being high BP. Waivers are available for SM with HTN who are controlled for at least 90 days. However, those with a cardiology/pulmonary medical waiver had an 80% higher risk of being medically evacuated while deployed at an approximate cost of $13,500 per patient. Uncontrolled HTN undermines the Department of Defense (DoD) mission of maintaining a medically ready force and promoting the health of all beneficiaries.

Figure 1:
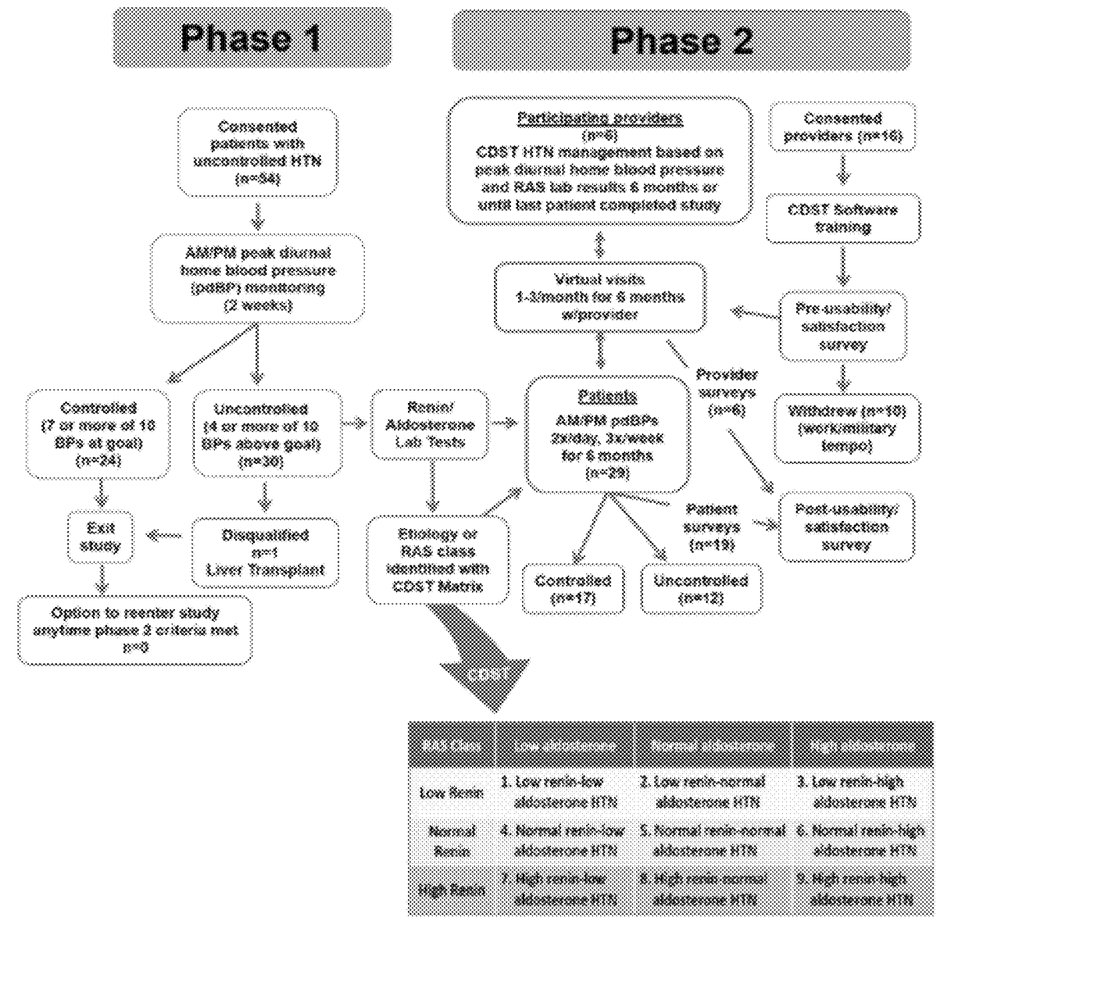
FIG. 1 (FIG. 1) is an schematic illustrating a single-arm pilot study protocol and RAS matrix which indicated that a clinical decision support tool described herein using peak diurnal blood pressure (pdBP) monitoring is a feasible option to facilitate improved rates of control in resistant hypertension (rHTN), aid in overcoming therapeutic/diagnostic inertia, and improve identification of secondary hypertension (sHTN).

Hypertension is most commonly defined as a BP consistently above a guideline recommended target. Equating elevated BP with a diagnosis of HTN, without further distinction, facilitates diagnostic inertia, causing HTN to be treated as a singular disease. However, there are over 50 secondary causes and underlying mechanisms for elevated BP. These include increased peripheral vascular resistance from endothelial dysfunction, central vasomotor control, or reduced renal blood flow, volume disturbances, epithelial sodium channel (ENaC) disease, renin and aldosterone abnormalities, monogenetic etiologies, tumors, adenomas, etc. Nosology, the science of disease classification, is critical for optimal control of any disorder. A diagnosis of "cancer" is not helpful as oat cell and squamous cell have different outcomes and treatments. High renin HTN from a renin producing tumor is different from high renin HTN from renal artery stenosis. Using a low, normal, high, renin-aldosterone classification matrix (FIG. 1) may help clinicians better describe HTN and identify secondary causes of HTN, such as Conn's syndrome, Cushing's syndrome, coarctation of the aorta, hypothyroidism, acromegaly, etc. Each category within the matrix has an extensive differential diagnosis, diagnostic criteria, and specific peer-reviewed treatments ranging from medication to surgery.

Further, anti-hypertensive medications have specific mechanisms of action. Matching the mechanism of HTN with the mechanism of the anti-hypertensive drugs has been advocated to improve BP control. Aldosterone antagonists are useful in high aldosterone HTN. Diuretics and calcium channel blockers are preferred in older patients with low renin-normal aldosterone HTN or low renin-low aldosterone HTN. Diuretics are preferred in high volume states and have different mechanisms of action and effects on BP. Thiazide diuretics work at the proximal tubule and are less effective in ENaC disease seen in low renin-low aldosterone HTN or low renin-normal aldosterone HTN. Here current data suggests amiloride or triamterene may be more effective. Diuretics may not have the same clinical outcomes in different populations. Variable mortality and stroke rates have been reported with chlorthalidone vs. hydrochlorothiazide vs. indapamide. Complex decisions such as these consume significant provider management time that can be optimized with clinical decision support tool (CDST).

Clinical decision support tools analyze patient data using evidence-based guidelines, informing providers' clinical judgment. By synthesizing literature and data from electronic medical records (EMRs) into manageable vignettes, CDSTs enable providers to quickly make evidence-based decisions, enhancing quality, safety, and communication, while standardizing care and facilitating virtual management. The dominant regulator of BP is the renin-aldosterone system (RAS). Over 45 years ago, a renin-aldosterone classification system was proposed to better define the mechanism of HTN, but little additional work has been performed to further develop this initial reporting. See, Laragh J H, Baer L, Brunner H R, et al: Renin, angiotensin and aldosterone system in pathogenesis and management of hypertensive vascular disease. Am J Med 1972; 52: 633-52. A recommendation was subsequently made to use renin levels to better manage HTN, and Egan et al. showed BP control could be improved using renin to differentiate capacitance vs. resistance states, suggesting that the field should consider pursing simpler tests of individual molecules as opposed to combinations of biological markers. See Egan B M, Basile J N, Rehman S U, et al: Plasma Renin test-guided drug treatment algorithm for correcting patients with treated but uncontrolled hypertension: a randomized controlled trial. Am J Hypertension 22(7): 792-801. Published online Apr. 16, 2009. 10.1038/ajh.2009.63. The prior art failed to suggest processes or systems that can integrate select biometric information of a subject in a clinical support tool for providing a differential diagnosis that sorts secondary HTN.

In some aspects, the disclosure provides a clinical support tool that processes a set of peak diurnal blood pressure measurements using a matrix for identifying subjects with resistant hypertension. In some instances, the systems and processes of the disclosure combine the pdBP measurements with input of renin-aldosterone test results to provide an extensive differential diagnosis of HTN. In some aspects, the systems and processes of the disclosure sort secondary HTN conditions from a multitude of other underlying factors. The systems of the disclosure can use a drug sequencing algorithm based on age, ethnicity, associated-disease, renin/aldosterone levels, and other factors to evaluate the effects on BP control, provider time, and provider/patient satisfaction. In specific embodiments, the systems of the disclosure can sort RAS distribution and disease distribution in a population.

Provided herein is a clinical decision support (CDS) system for a subject afflicted by resistant hypertension, the CDS system comprising a non-transitory computer readable medium storing instructions that, when executed by at least one programmable processor, cause the at least one programmable processor to perform operations comprising: receiving, by a computing device, a set of data consisting of at least five blood pressure measurements of the subject; classifying the data into one of two bins consisting of controlled or uncontrolled by a computer implemented method selected from a linguistic method and a machine learning method; and outputting the classification result, thereby providing clinical decision support for the identification of resistant hypertension in the subject. In some cases, the system further comprises receiving, by a computing device, a result from a renin test of the subject, an aldosterone test of the subject, or both. In some cases, the data is further structured by a matrix that groups the results from the renin test of the subject and the result from the aldosterone test of the subject into one of nine-possible combinations of low, normal, and high renin and aldosterone levels. Preferably, each category of the nine-possible combinations of low, normal, and high renin and aldosterone levels is associated with a differential diagnosis of hypertension.

Hypertension Clinical Decision Support Tool (CDST)

The present disclosure describes systems and process for managing hypertension using a clinical decision support tool (CDST). The disclosure also illustrates an application of some of its embodiments by providing the results of a clinical study that determined feasibility and validated the efficacy of a CDST for assisting providers with the diagnosis and management of uncontrolled or resistant HTN (rHTN). In some instances, the systems and processes described herein improve rates of BP control among patients heretofore uncontrolled with usual care.

In many instances, primary outcomes obtained with the systems and methods of the disclosure include significant improvement of: 1) BP rates as compared to control groups; 2) provider management time using an electronic logbook; and 3) satisfaction with the CDST.

The systems and methods of this disclosure may comprise a treatment method to manage a controlled or uncontrolled hypertension of a subject. In some cases the hypertension is resistant hypertension. Subjects can be humans, non-human primates such as chimpanzees, and other domesticated animals such as dogs and cats. A subject can be of any age. Subjects can be, for example, elderly adults, adults, adolescents, pre-adolescents, children, toddlers, infants.

Digital Processing Device

In some aspects, the disclosed provides a clinical decision support tool to manage hypertension, preferably resistant hypertension, in one or more subjects. In many instances, systems, platforms, software, networks, and methods described herein include a digital processing device, or use of the same. In further embodiments, the digital processing device includes one or more hardware central processing units (CPUs), i.e., processors that carry out the device's functions, such as receiving an input from a peak diurnal blood pressure measurement, or an input from renin-aldosterone test. The CDST system disclosed herein or a computer system used in the analyses of a set of pdBPs, renin test results, aldosterone test results, can share the results with a third-party from any other facility, such as a hospital a clinical or another. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In other embodiments, the digital processing device could be deployed on premise or remotely deployed in the cloud.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art. In many aspects, the disclosure contemplates any suitable digital processing device that can either be deployed to a subjects home or dwelling for on-site monitoring, or is used within a health care facility to process and analyze a variety of measurements. In some instances, measurements are done in multiple places as guidelines suggest office-based BP readings above goal should be verified by home-based readings, as 29% to 39% of apparent resistant HTN (aHTN) will have white coat Syndrome/pseudo-rHTN (high in office, normal at home). A smaller number of people will have masked HTN (low in health care office/facility and high at home).

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. In the specific Examples provided herein, the data was analyzed using IBM SPSS version 24.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a third-party, such as health care facility, a physicians office, or a relative of the subject being monitored for hypertension. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280×about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia. In specific instances, such images can become part of the subjects medical record.

Non-Transitory Computer Readable Storage Medium

In many aspects, the systems, processes, software, networks, and methods that provide the clinical decision support tool disclosed herein include one or more non-transitory computer readable storage media encoded with a program including instructions executable by the operating system of an optionally networked digital processing device. For instance, in some aspects, the methods comprise creating data files associated with a plurality of pdBP measurements from a set of data. In preferred embodiments, the set of data is received over a period-of-time at regular intervals, such as consecutive days. The regular intervals can be selected from daily, twice-daily, weekly, or biweekly, monthly, and bimonthly, but in most preferred embodiments the regular intervals are daily or twice-daily. In some cases, the period-of-time is over a course of at least 2 days, at least 5 days, at least 10 days, or at least 14 days, or another suitable time frame that supports management of hypertension in the subject. For instance, the suitable period of time can be throughout the lifetime of the subject. In specific instances, the set of data comprises at least two peak diurnal blood pressure measurements, such as a peak morning blood pressure measurement (peak am) and a peak afternoon blood pressure measurement (peak pm). In other instances, the set of data comprises a peak morning blood pressure measurement from day 1 and a peak morning blood pressure measurement from day 2. A plurality of pdBP measurements can be provided for a plurality if days, such as day 1, day 2, day 3, day 4, day 5, day 6, day 7, day 8, day 9, day 10, day 11, day 12, day 13, day 14, or another suitable number of days. The non-transitory computer storage medium can store data files associated all of the measurements described herein.

Further the systems, processes, software, networks, and methods that provide the clinical decision support tool disclosed herein include one or more non-transitory computer readable storage media encoded with a program including instructions executable by the operating system of an optionally networked digital processing device configured to create data files associated with a plurality of test results (and associated data measurements) measurements from a renin test of the subject, an aldosterone test of the subject, or both. In preferred embodiments, the data is further structured by a matrix that groups the results from the renin test of the subject and the result from the aldosterone test of the subject into one of nine-possible combinations of low, normal, and high renin and aldosterone levels. In combination with the measurements of pdBP the input from the nine-possible combinations of low, normal, and high renin and aldosterone levels can provide a differential diagnosis of hypertension. In additional embodiments, the data is further structured as to provide a listing of one or more drugs for one or more of the differential diagnosis of hypertension. The non-transitory computer storage medium can store data files associated with all of the measurements described herein.

In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media. Such computer readable storage medium is also suitable for storing the set of data contemplated by the disclosure.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein. It is specifically contemplated that the disclosed clinical decision support tool is configured for display on a mobile device. In specific instances, the CDST sends results for display on a graphical user interface. See FIG. 1 for an illustration. In preferred instances, the result comprises one or a combination of two or more of text, color, imagery, or sound to alert the subject or a care taker of a change in hypertension status of the subject. Specifically, the outputting operation can send an alert to an end-user if the results of the classification are "uncontrolled" and the subject had a previous result of "controlled."

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EXAMPLE

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The following experiments describe a single-arm pilot study used to evaluate the performance of the systems and process described herein.

Example 1. Design/Setting

This was a 2-phase, prospective, non-randomized, single-arm, 6-month pilot study conducted in primary care clinics at a tertiary military medical center (TMC) in the USA from May 2017 through July 2018; a facility with over 29,600 outpatient HTN visits yearly.

Participants

Patients and providers were recruited. Patient eligibility criteria were aged 18 years or older, cognitively intact, able to consent, and taking three or more antihypertensive medications for more than 1 month. Patient exclusion criteria were night-shift workers (because of limited evidence as to when to measure their diurnal highs), those unable to give valid informed consent in English, pregnant or breast-feeding women, prisoners, patients on renal dialysis, transplant patients, patients with chronic disease and a life expectancy less than 1 year. Active duty patients and providers transferring or deploying during the study were ineligible.

Providers were eligible if they were full time TMC employees with current credentials and prescribing privileges. Medical students and providers assigned temporarily at the TMC were ineligible.

All participants completed a demographic questionnaire. Patients received instruction on the importance of BP control, information regarding BP-friendly lifestyles, and proper technique for obtaining home BPs using a study-provided, digital BP monitor with an appropriate-sized arm cuff. Blood pressures were taken 3 days per week at a consistent time of day of their choosing between 8 AM and noon and 4 PM and 8 PM, the potential highest readings of the day (morning surge and chronotherapy trough). Baseline readings, the first 10 home readings taken over 10 days, were used to determine phase 2 eligibility. If 4 or more baseline readings were above recommended individualized JNC 8 BP goals set by their primary care provider (PCP), patients met criteria for rHTN and were enrolled in phase 2. See James P A, Oparil S, Carter B L, et al: 2014 Evidence-based guideline for the management of high blood pressure in adults—report from the panel members appointed to the eighth Joint National Committee (JNC8). JAMA 2014; 311(5): 507-20; describing BP goals. Control was defined as 70% or more of BP readings at goal. Phase 1 patients (usual care) meeting phase 2 (CDST augmented management) criteria for rHTN acted as their own controls. Patients were not screened for secondary causes of HTN before entering phase 2. Phase 2 patients were systematically screened for secondary causes of HTN using the CDST's diagnostic matrix.

Phase 2 patients continued checking BPs as in phase 1 and had morning renin and aldosterone levels drawn while on their current medications. If aldosterone was significantly elevated (>20 ng/dL) and/or the aldosterone-renin ratio (ARR) was over 25, a 3-week drug wash out interval and repeat labs were recommended in the matrix for the work up of primary aldosteronism. See Kline G A, Prebtani A P H, Leung A A, Ernesto L, Schiffrin E L: Primary aldosteronism: a common cause of resistant hypertension. CMAJ 2017; 189(22): E773-8. 10.1503/cmaj.161486; and see also Funder J W, Carey R M, Mantero F et al: The management of primary aldosteronism: case detection, diagnosis, and treatment: an endocrine society clinical practice guideline. J Clin Endocrinol Metab 2016; 101(5): 1889-916; describing treatments. Because of institutional review board stipulations, the actual workup for primary aldosteronism or other secondary causes of rHTN was managed by patients' PCP. Electrolytes were drawn as indicated. Study team members were available to answer questions and troubleshoot issues with the sphygmomanometer or website. At the end of 6 months, participants filled out a usability and satisfaction survey.

Providers participated in phase 2 only. After an initial in-person visit, providers monitored readings, lab work, and adjusted medications virtually, using the web-based CDST with templated virtual visits (W) using point and click lab and medication ordering. Each provider kept a daily logbook within the CDST that measured the number of patients man-aged and total minutes spent on W daily. Average visit time for each provider was automatically calculated in the CDST. Estimates of time variance were calculated by comparing the average W time to the TMC's standard 20-minute office visit. Other standard of care interventions during the W were at the discretion of the managing provider according to usual care.

Example 2. Interventions

Interventions administered in this study included 1) peak diurnal home BP monitoring (peak diurnal blood pressure [pdBP]), 2) CDST evaluation and manage-ment, and 3) templated W to replace face-to-face office vis-its. Resistant HTN in this study followed the 2018 American Heart Association criteria: BP above goal on three maximally tolerated medications, one of which was a diuretic for at least 1 month.

Example 3. Instruments/Measures

Blood Pressure Measurements

Guidelines suggest office-based BP readings above goal should be verified by home-based readings, as 29% to 39% of apparent resistant HTN (aHTN) will have white coat syndrome/pseudo-rHTN (high in office, normal at home). A smaller number of people will have masked HTN (low in office and high at home). To ensure only participants with rHTN received the intervention, we had consented patients follow their usual medical plan of care while doing pdBP for 2 weeks (10 baseline readings) using an OMRON 10 Bluetooth digital BP monitor. Peak diurnal BP readings were taken 3 days per week at a consistent time of day for each patient. This strategy was expected to decrease temporal variation in measurement and increase the probability of measuring the highest readings of the day to avoid missing masked HTN.

We used the concept of BP Load (the percent of the time spent above individualized target BPs) to help define the presence or absence of HTN and rate of control. Patients meeting phase 2 inclusion criteria were followed for 6 months. Control was defined as both systolic and diastolic BP within goal. Phase 1 patients found to have aHTN were encouraged to continue monitoring home BPs and contact study person-nel if their BP was consistently above goal. They could then enroll in phase 2.

We did not formally measure medication adherence in phase 2 patients. If they were controlled, it did not matter, and if they were not adherent, it was considered a failure of the CDST. The follow-up every 10 days was designed to overcome diagnostic/therapeutic inertia and promote ongoing patient participation, which may improve adherence or at least detect nonadherence.

Example 4. Clinical Decision Support Tool (CDST)

The CDST was designed to address six major problems with BP control: 1) compliance with every 10-day monitoring, 2) lifestyle behaviors with educational materials, 3) diagnostic inertia using the diagnostic matrix below, 4) therapeutic iner-tia using the drug algorithm below, 5) definition by using pdBP monitoring, and 6) provider interface time using VV.

Renin-aldosterone Classification Matrix

This matrix derives from the nine-possible combinations of low, normal, and high renin and aldosterone levels. These range from low renin-low aldosterone HTN (box 1, rare monogenetic etiologies) to high renin-high aldosterone HTN (box 9, secondary hyperaldosteronism). Primary HTN falls in the normal renin-normal aldosterone HTN category, box 5 (see FIG. 1). Each category (1-9) has an extensive differential diagnosis with associated therapy accessed by clicking on the box and reading the text. For example, if the patient had low renin-high aldosterone HTN (box 3) with an ARR above 25, after a 3-week drug wash out, the differential diagnosis would include: Conn's syndrome (because of bilat-eral adrenal hyperplasia, aldosterone producing adenoma, unilateral adrenal hyperplasia, familial hyperaldosteronism 1-2-3), adrenocortical carcinomas, ectopic aldosterone secreting tumors, simple virilizing form of partial 21-hydroxylase enzyme deficiency congenital adrenal hyperplasia, and a list of drugs that raise aldosterone or lower renin. Some of these have surgical options and control depends on differentiation.

Drug Sequencing Algorithm

Sequencing was determined by current guidelines and literature recommendations based on age, ethnicity, associated disease, renin-aldosterone levels, and patient tolerance. For example, patients over age of 60 years would be sequenced to a diuretic followed by a calcium channel blocker as recommended by the 2018 guidelines. For Black patients, another sequencing scheme would be displayed. Black patients have a high percentage of low renin-normal aldosterone primary HTN (box 2) and thiazide diuretics are specifically recommended for these patients followed by calcium channel blockers. However, up to 6% of rHTN in Blacks is related to ENaC disease that often responds better to amlodipine or triamterene. If patient ethnicity was reported as Black, the sequence would read: thiazide diuretic, if uncontrolled add or substitute amiloride or triamterene, then if uncontrolled add a calcium channel blocker, all adjusted to maximum tolerated dosing.

Perceived Usefulness/Satisfaction

A 20-item technology acceptance questionnaire based on the technology acceptance model was developed for this study. Development is reported elsewhere. Responses on a 7-point Likert scale ranged from likely to unlikely. Responses for the 5-point scale ranged from never to always. Sample provider questions were: "Using this software in my job increased my productivity." "The software provided sufficient clinical information for me." "The software was user friendly." Patient questions were similar: "Using this software made it easier to manage my blood pressure." "The information content of the software met my needs." "It was easy for me to become good at using this software."

Statistical Methods

Data were analyzed using IBM SPSS version 24. Descriptive statistics were used with all variables. The Kolmogorov-Smirnov and Shapiro goodness-of-fit tests were run to check for normalcy of distribution. Because of the small sample size, the two-sided Fisher Exact test was run as appropriate.

Results

Demographics

After receiving institutional review board approval, 54 patients who were uncontrolled with usual care and met inclusion criteria were consented and enrolled into phase 1. Of these, one participant was found to be ineligible because of a history of liver transplant, 24 (45.3%) were determined to have aHTN using pdBP monitoring, and 29 met phase 2 crite-ria for rHTN. There were no significant demographic differ-ences between phase 1 and phase 2 participants. The majority of phase 2 patients were married (n=23), male (n=19), with an average age of 69.6 years, almost half (n=14) were diabetic, and one was active duty (Table I). For statistical analysis, ethnicity was categorized as white (n=22) and other (n=7). Goal BP for 27 patients was 140/90 and 150/90 for 2 patients over age 65. No phase 1 patients identified as having aHTN, subsequently met phase 2 criteria and reentered the study. Sixteen PCPs volunteered and were consented. Three physicians and three nurse practitioners completed the study.

TABLE I

Selected Patient Characteristics by Study Phase
Table I. Selected Patient Characteristics by Study Phase

| | Phase 1 (aHTN) (N = 24) | | Phase 2 (rHTN) (N = 29) | | |
|---|---|---|---|---|---|
| Factor | N | Percent | N | Percent | Fisher's exact Test |
| Male | 12 | 50 | 19 | 65.5 | 0.278 |
| Female | 12 | 50 | 10 | 34.5 | 0.278 |
| White | 12 | 50 | 22 | 75.9 | 0.084 |
| Other | 12 | 50 | 7 | 24.1 | 0.084 |
| History of Diabetes | 9 | 37.5 | 14 | 48.3 | 0.579 |
| History of OSA | 11 | 45.8 | 11 | 37.9 | 0.588 |
| Tobacco current | 12 | 50 | 13 | 41.4 | 0.785 |
| Alcohol Yes | 11 | 45.8 | 14 | 48.3 | 1.0 |
| Family history of HTN | 15 | 62.5 | 11 | 37.9 | 0.101 |

| | Phase 1 (aHTN) (N = 24) | | | | Phase 2 (rHTN) (N = 29) | | |
|---|---|---|---|---|---|---|---|
| | Mean | Std | Range (min-max) | Sig* [95% CI] | Mean | Std | Range (min-max) |
| Age (years) | 60.21 | 11.68 | 31-82 | 0.002 [−14.98-3.71] | 69.55 | 8.7 | 32 (53-85) |
| BMI | 32.7 | 4.57 | 27-44 | 0.53 [−1.99-3.81] | 31.8 | 5.72 | 25.39 (21.6-47) |
| Renin (ng/mL/h) | | | | | 3.23 | 4.96 | 22.05 (0.0-22.05) |
| Aldosterone (ng/dL) | | | | | 8.82 | 7.8 | 27.8 (0.21-28) |
| ARR (ng/dL) | | | | | 21.64 | 53.5 | 279.97 (0.03-280) |

*$P < 0.05$.
Other represents Black, Asian, Pacific Islander, Native American, or Hispanic.
aHTN = apparent/white coat HTN; ARR = aldosterone-renin ratio; BMI = body mass index; HTN = hypertension; NA = not applicable; OSA = obstructive sleep apnea; ng/mL/h = nanograms per milliliter per hour; ng/dL = nanograms per deciliter; rHTN = resistant HTN.

Time Management and Treatment Decisions fastest provider averaged 10 minutes per patient. The slowest provider was 20.56 minutes. The overall average was 16.59 minutes (17.05% less time spent), saving 3.41 minutes per office visit avoided. Using home dpBP monitoring, 24 (45%) of 53 patients followed regularly in the clinic for "uncontrolled HTN" were misclassified as they had aHTN. Once recognized as controlled, they no longer needed frequent HTN follow-up clinic visits.

Diagnostics

Renin and aldosterone abnormalities were identifiedin 69% (n=20) of participants (see Table II). No patients had high renin HTN (Boxes 7,8,9). Per study protocol, all patients with abnormal renin-aldosterone levels requiring diagnostic workup (n=3) were referred to their PCP. No adverse events, e.g., electrolyte imbalances occurred during the study.

TABLE II

Selected Phase 2 Patient Characteristics: Controlled vs. Uncontrolled
TABLE II. Selected Phase 2 Patient Characteristics: Controlled vs. Uncontrolled

| | Uncontrolled (N = 12) | | Controlled (N = 17) | | |
|---|---|---|---|---|---|
| Factor | N | Percent | N | Percent | Fisher's exact test (2-sided) |
| Male | 7 | 58.3 | 12 | 70.6 | 0.69 |
| Female | 5 | 41.7 | 5 | 29.4 | 0.69 |
| White | 7 | 58.3 | 15 | 88.2 | 0.09 |
| Other | 5 | 41.7 | 2 | 11.8 | 0.09 |
| History of diabetes | 9 | 75.0 | 5 | 29.4 | 0.025 |
| History of OSA | 6 | 50.0 | 5 | 29.4 | 0.44 |
| Tobacco (current) | 4 | 33.3 | 9 | 52.9 | 0.45 |
| Alcohol (current) | 3 | 25.0 | 11 | 64.7 | 0.06 |
| Family history of HTN | 6 | 50.0 | 5 | 29.4 | 0.47 |
| Box 1: low renin-low aldosterone aldosterone | 3 | 25 | 1 | 5.9 | 0.28 |
| Box 2: low renin-normal aldosterone | 2 | 16.6 | 7 | 41.2 | 0.23 |
| Box 3: low renin-high aldosterone | 3 | 25 | 1 | 5.9 | 0.28 |
| Box 4: normal renin-low aldosterone | 1 | 8.3 | 2 | 11.8 | 0.45 |
| Box 5: primary HTN | 3 | 25 | 6 | 35 | 0.69 |

| | Uncontrolled | | | Sig.* | Controlled | | |
|---|---|---|---|---|---|---|---|
| | Mean | Std | Range | 95% CI | Mean | Std | Range |
| Age (years) | 68.56 | 7.5 | 26 | 0.41 [−4.035-9.545] | 70.77 | 10.22 | 32 |
| BMI | 31.61 | 4.51 | 15 | 0.86 [−4.114-4.896] | 32.05 | 7.13 | 25.39 |
| Renin (ng/mL/h) | 3.03 | 4.07 | 15.6 | 0.94 [−3.756-4.065] | 3.46 | 6.06 | 22.5 |
| Aldosterone (ng/dL) | 7.86 | 6.34 | 25.9 | 0.5 [−4.044-8.079] | 9.992 | 9.36 | 27 |
| ARR (ng/dL) | 13.57 | 19.59 | 63.63 | 0.29 [−20.117-64.682] | 32.39 | 79.2 | 279.6 |

*$P < 0.05$.
Other represents Black, Asian, Pacific Islander, Native American, or Hispanic.
aHTN = apparent/white coat HTN; ARR = aldosterone-renin ratio; BMI = body mass index; HTN = hypertension; NA = not applicable; OSA = obstructive sleep apnea; ng/mL/h = nanograms per milliliter per hour; ng/dL = nanograms per deciliter; rHTN = resistant HTN.

Rates of Control

Change in rates of control, both systolic and diastolic, were statistically significant (P=0.005) at 2, 4, and months, 24.1%, 44.8%, and 58.6%, respectively, with higher rates of control among males (58%) than females (50) at 6 months. Number to treat was less than 2. Compared with baseline, there was an 11 mm Hg reduction in AM systolic readings and a 9 mm Hg (9.9%) reduction in AM diastolic readings at 6 months. Afternoon systolic BPs fell 31 mm Hg (17.1%) and PM diastolic BP fell mm Hg (9.9 at 6 months (Table I). At 6 months the average AM BP was 134/74 and the aver-age PM BP was 132/72 in the controlled group. At months, the uncontrolled group had an average AM pressure of 145/76 and an average PM pressure of 152/79. Diabetes was the only significant variable associated with the uncontrolled group (Table II). If the aHTN phase 1 group is included, the overall study rate of control rises to 77% (n=41).

TABLE III

Percent of Change in Selected AM-PM Blood Pressures From Baseline
TABLE III Percent of Change in Selected AM-PM Blood Pressures From Baseline

| | Baseline | | | | 6 months | | | | % change | % change |
|---|---|---|---|---|---|---|---|---|---|---|
| | Controlled | | Uncontrolled | | Controlled | | Uncontrolled | | Controlled | Uncontrolled |
| | SBP | DBP | SBP | DBP | SBP | DBP | SBP | DBP | Sys/Dias | Sys/Dias |
| Highest AM | 165 | 91 | 165 | 104 | 154 | 82 | 163 | 102 | 6.7/9.9 | 1.9/1.9 |
| Highest PM | 181 | 92 | 176 | 105 | 150 | 83 | 173 | 102 | 17.1/9.8 | 2.9/2.9 |
| Average AM | 150 | 83 | 152 | 82 | 134 | 74 | 145 | 76 | 10.7/10.8 | 7.3/7.3 |
| Average PM | 146 | 80 | 154 | 82 | 132 | 72 | 152 | 79 | 9.6/10 | 3.7/3.7 |
| Lowest AM | 136 | 81 | 134 | 62 | 115 | 63 | 132 | 54 | 15.4/22.2 | 14.9/12.9 |
| Lowest PM | 138 | 78 | 124 | 60 | 115 | 61 | 139 | 41 | 16.6/21.8 | 12.1/31.6 |

DBP = diastolic blood pressure;
SBP = systolic blood pressure.

Perceived Feasibility/Satisfaction

Provider (n=6) responses indicated that perceived usefulness was favorable, ease of use slightly favorable. Patient (n=19) perceived usefulness and ease of use were both favorable.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. A clinical decision support (CDS) system for a subject afflicted by resistant hypertension, the CDS system comprising
    a non-transitory computer readable medium storing instructions that, when executed by at least one programmable processor, cause the at least one programmable processor to perform operations comprising:
    receiving, by a computing device, a set of data consisting of at least five blood pressure measurements of the subject, a result from a renin test of the subject, a result from an aldosterone test of the subject;
    causing the result of the renin test and the result of the aldosterone test to by structured into a matrix having one of nine-possible combinations of low, normal, and high renin and aldosterone levels whereby the matrix is trained by machine learning methods on a training set of classifiers from a population of subjects afflicted with hypertension for classifying each of the nine-possible combinations and the at least five blood pressure measurements of the subject with at least 70 possible differential diagnosis of hypertension; and
    outputting the at least 70 possible differential diagnosis of hypertension classification result, applying a drug sequencing algorithm to the at least 70 possible differential diagnosis of hypertension to generate a listing of one or more drugs for the at least 70 possible differential diagnosis of hypertension;
    outputting the listing of one or more drugs for the at least 70 possible differential diagnosis of hypertension;
    thereby providing clinical decision support for the identification of resistant hypertension in the subject.

2. The system of claim 1, wherein the data is further structured as to provide a listing of one or more drugs for each specific differential diagnosis of hypertension.

3. The system of claim 1, wherein the one or more differential diagnosis of hypertension for a low renin-high aldosterone combination is selected from the group consisting of: Conn's syndrome, aldosterone producing adenoma, unilateral adrenal hyperplasia, familial hyperaldosteronism 1-2-3), adrenocortical carcinomas, ectopic aldosterone secreting tumors, simple virilizing form of partial 21-hydroxylase, and enzyme deficiency congenital adrenal hyperplasia.

4. The system of claim 1, wherein the one or more differential diagnosis of hypertension for a low renin-normal aldosterone combination is selected from the group consisting of: Chronic Kidney Disease, Low renin primary HTN, Syndrome of Supine HTN-OH, and Pheochromocytoma.

5. The system of claim 1, wherein the one or more differential diagnosis of hypertension for a low renin-low aldosterone combination is selected from the group consisting of: Congenital Adrenal Hyperplasia due to 11β-hydroxylase (CYP11B1) deficiency), Congenital Adrenal Hyperplasia due to 17α-hydroxylase (CYP17) deficiency, DOC producing Tumors, 18-Hydroxy-ll-deoxycorticosterone (18-OH-DOC) aldosteronoma, Mineralocorticoid receptor activating mutation, Geller's Syndrome, Pregnancy exacerbated hypertension, Pseudohypoaldosteronism Type II/PHA II, Gordon's Syndrome, Chloride shunt syndrome, Mineralocorticoid resistant hyperkalemia, Kidney Disease (Glomerular or Tubular disease), Liddle's Syndrome, Pseudohypoaldosteronism Type II/PHA II, Weinstein-Spitzer Syndrome, Subtype 3 Renal Tubular Acidosis, Medication Effect (NSAIDs, Cox 2 inhibitors), Pheochromocytoma, Adducin Polymorphism, Endogenous Ouabain, Exogenous Source, GIP induced Cushing's, Cushing's Disease, Cushing's Syndrome, Iatrogenic Cushing's, Syndrome, Pan-neoplastic Cushing's syndrome, Generalized Glucocorticoid Resistance (Chrousos Syndrome), Congenital Apparent Mineralocorticoid Excess (AME), Acquired AME/Pseudohyperaldosteronism, Small cell cancer of the lung (éACTH), Bronchial carcinoids (éACTH), and Pheochromocytoma.

6. The system of claim 1, wherein the one or more differential diagnosis of hypertension for a normal renin-low aldosterone combination is selected from the group consisting of: Congenital Adrenal Hyperplasia due to 11β-hydroxylase (CYP11B1) deficiency), Congenital Adrenal Hyperplasia due to 17α-hydroxylase (CYP17) deficiency, DOC producing Tumors, 18-Hydroxy-ll-deoxycorticosterone (18-OH-DOC) aldosteronoma, Mineralocorticoid receptor activating mutation, Geller's Syndrome, Pregnancy exacerbated hypertension, Pseudohypoaldosteronism Type II/PHA II, Gordon's Syndrome, Chloride shunt syndrome, Mineralocorticoid resistant hyperkalemia, Kidney Disease (Glomerular or Tubular disease), Liddle's Syndrome, Pseudohypoaldosteronism Type I/PHA II, Weinstein-Spitzer Syndrome, Subtype 3 Renal Tubular Acidosis IV, Medication Effect (NSAIDs, Cox 2 inhibitors), Pheochromocytoma, Adducin Polymorphism, Endogenous Ouabain, Exogenous Source, GIP induced Cushing's, Cushing's Disease, Cushing's Syndrome, Iatrogenic Cushing's Syndrome, Pan-neoplastic Cushing's syndrome, Generalized Glucocorticoid Resistance (Chrousos Syndrome), Chrorous Syndrome, Congenital Apparent Mineralocorticoid Excess (AME), Acquired AME/Pseudohyperaldosteronism, Small cell cancer of the lung (éACTH & cortisol), Bronchial carcinoids (éACTH & cortisol), Pheochromocytoma.

7. The system of claim 1, wherein the one or more differential diagnosis of hypertension for a normal renin-normal aldosterone combination is selected from the group consisting of: Acromegaly, AD HTN with brachydactyly, Drugs, Hyperparathyroidism, Hyperthyroidism, Hypoparathyroidism, Hypothyroidism, Increased Intercranial Pressure, Insomnia, Sleep Apnea, Primary/Essential HTN, and Pheochromocytoma.

8. The system of claim 1, wherein the one or more differential diagnosis of hypertension for a normal renin-high aldosterone combination is selected from the group consisting of: APA/Conn's Syndrome, Bilateral Adrenal Hyperplasia, Unilateral Adrenal Hyperplasia, Ectopic Aldosterone Tumor, Familial Hyperaldosteronism 1, Familial Hyperaldosteronism 2, Familial Hyperaldosteronism 3, and Pheochromocytoma.

9. The system of claim 1, wherein the one or more differential diagnosis of hypertension for a high renin-low aldosterone combination is selected from the group consisting of: Coarctation of the Aorta, Diabetic Nephropathy, Glomerulonephritis, Glomerulosclerosis, Middle Aortic Syndrome, Polycystic Kidneys, Renal artery Fibromuscular Hyperplasia, Renal Artery Dissection, Renal Artery Emboli/Infarction, Renal Artery Stenosis, Renin secreting Tumors, Takayasu's Arteritis, and Pheochromocytoma.

10. The system of claim 1, wherein the one or more differential diagnosis of hypertension for a high renin-normal aldosterone combination is selected from the group consisting of: Coarctation of the Aorta, Diabetic Nephropathy, Glomerulonephritis, Glomerulosclerosis, Middle Aortic Syndrome, Polycystic Kidneys, Renal artery Fibromuscular Hyperplasia, Renal Artery Dissection, Renal Artery Emboli/Infarction, Renal Artery Stenosis, Renin secreting Tumors, Takayasu's Arteritis, and Pheochromocytoma.

11. The system of claim 1, wherein the one or more differential diagnosis of hypertension for a high renin-high aldosterone combination include: Coarctation of the Aorta, Diabetic Nephropathy, Glomerulonephritis, Glomerulosclerosis, Middle Aortic Syndrome, Polycystic Kidneys, Renal artery Fibromuscular Hyperplasia, Renal Artery Dissection, Renal Artery Emboli/Infarction, Renal Artery Stenosis, Renin secreting Tumors, Takayasu's Arteritis, Toxemia of Pregnancy, and Pheochromocytoma.

12. The system of claim 1, wherein the set of data is received at regular intervals.

13. The system of claim 12, wherein the regular intervals are selected from daily, twice-daily, weekly, or biweekly, monthly, and bimonthly.

14. The system of claim 1, wherein the set of data is received over a period-of-time.

15. The system of claim 14, wherein the period-of-time is over a course of at least 2 days, at least 5 days, at least 10 days, or at least 14 days.

16. The system of claim 1, wherein the set of data comprises at least two peak diurnal blood pressure measurements.

17. The system of claim 16, wherein the at least two peak diurnal blood pressure measurements comprise an average peak diurnal blood pressure measurement (peak am) and an average peak afternoon blood pressure measurement (peak pm).

18. The system of claim 16, wherein the at least two peak diurnal blood pressure measurements in the at least six peak diurnal blood pressure measurements comprises a peak morning blood pressure measurement from day 1 and a peak morning blood pressure measurement from day 2.

19. The system of claim 16, wherein the at least six peak blood pressure measurements are from consecutive days.

20. The system of claim 1, providing by a computing device, the set of data consisting of blood pressure measurements of the subject to a health care provider.

21. The system of claim 1, wherein the at least one programmable processor is configured to query a database of electronic records to retrieve an age, an ethnicity, or a weight, or the subject.

22. The system of claim 21, further comprising using h drug sequencing algorithm based on age, ethnicity, and one of nine-possible combinations of low, normal, and high renin and aldosterone levels from the subject for annotating the set of data with a differential diagnosis for secondary hypertension.

23. The system of claim 1, wherein the listing of one or more drugs is displayed on a graphical user interface.

24. The system of claim 23, wherein the listing of one or more drugs comprises one or a combination of two or more of text, color, imagery, or sound.

25. The system of claim 23, wherein the alert is in the form of a visual or audio signal that is transmitted to a computing device selected from a personal computer, a tablet computer, and a smart phone.

26. The system of claim 23, wherein the alert is manifested as any of an email, a text message, a voice message, or sound.

27. A system comprising the CDS system of claim 1 operatively linked to one or more databases of electronic medical records or clinical data, or both.

28. The system of claim 1, further comprising administering a drug from the listing of one or more drugs for the at least 70 possible differential diagnosis of hypertension of hypertension to the subject.

* * * * *